United States Patent
Zheng et al.

(10) Patent No.: US 11,210,783 B2
(45) Date of Patent: Dec. 28, 2021

(54) METHOD AND DEVICE OF PROCESSING PLAQUES IN MAGNETIC RESONANCE IMAGING OF VESSEL WALL, AND COMPUTER DEVICE

(71) Applicant: SHENZHEN INSTITUTES OF ADVANCED TECHNOLOGY, Shenzhen (CN)

(72) Inventors: Hairong Zheng, Shenzhen (CN); Xin Liu, Shenzhen (CN); Na Zhang, Shenzhen (CN); Zhanli Hu, Shenzhen (CN); Dong Liang, Shenzhen (CN); Yongfeng Yang, Shenzhen (CN)

(73) Assignee: Shenzhen Institutes of Advanced Technology, Shenzhen (CN)

( * ) Notice: Subject to any disclaimer, the term of this patent is extended or adjusted under 35 U.S.C. 154(b) by 16 days.

(21) Appl. No.: 16/910,074

(22) Filed: Jun. 24, 2020

(65) Prior Publication Data

US 2020/0320704 A1    Oct. 8, 2020

Related U.S. Application Data

(63) Continuation-in-part of application No. PCT/CN2019/078890, filed on Mar. 20, 2019.

(30) Foreign Application Priority Data

Jul. 24, 2018    (CN) .......................... 201810818827.1

(51) Int. Cl.
*G06K 9/00*    (2006.01)
*G06T 7/00*    (2017.01)
(Continued)

(52) U.S. Cl.
CPC .......... *G06T 7/0012* (2013.01); *G06K 9/6256* (2013.01); *G06K 9/6267* (2013.01);
(Continued)

(58) Field of Classification Search
CPC .......... G06K 2209/051; G06K 9/6256; G06K 9/6267; G06N 3/0454; G06N 3/0472;
(Continued)

(56) References Cited

U.S. PATENT DOCUMENTS

| 2005/0043614 A1* | 2/2005 | Huizenga ................. C23F 11/08 |
| | | 600/427 |
| 2019/0122120 A1* | 4/2019 | Wu ....................... G06N 3/0472 |
| 2019/0333198 A1* | 10/2019 | Wang ................... G06N 3/0454 |

FOREIGN PATENT DOCUMENTS

| CN | 107871318 A | 4/2018 |
| CN | 108229381 A | 6/2018 |

OTHER PUBLICATIONS

CapsuleGAN: Generative Adversarial Capsule Network; Ayush Jaiswal, Wael AbdAlmageed, Premkumar Natarajan USC Information Sciences Institute; Marina del Rey, CA; arXiv:1802.06167v1; Feb. 17, 2018; 6 pages.

(Continued)

*Primary Examiner* — Xin Jia
(74) *Attorney, Agent, or Firm* — Robert L. Stearns; Dickinson Wright, PLLC

(57) ABSTRACT

A method of processing plaques in magnetic resonance imaging of vessel wall include: step S101, training a generative adversarial network and a capsule neural network to obtain a trained generator network and a trained capsule neural network; and step S102, cascade-connecting the trained generator network with the capsule neural network into a system to recognize and classify plaques in magnetic resonance imaging of vessel wall. In one aspect, the capsule neural network has more abundant vascular plaques characteristic information represented by vector; in another aspect, when the trained generator network and the capsule neural network are cascaded into the system to recognize and classify the plaques in magnetic resonance imaging of
(Continued)

Training a generative adversarial network and a capsule neural network to obtain a trained generator network and a trained capsule neural network — Step 101

Cascade-connecting the trained generator network with the capsule neural network into a system so as to recognize and classify plaques in the magnetic resonance imaging of vessel wall — Step 102 vessel wall, an accuracy of recognition and classification may be greatly improved. A device for processing the method as well as a computer for implementing are also disclosed.

4 Claims, 1 Drawing Sheet

(51) Int. Cl.
  *G16H 30/40*    (2018.01)
  *G06K 9/62*    (2006.01)
  *G06N 3/08*    (2006.01)
  *G06T 11/00*    (2006.01)

(52) U.S. Cl.
  CPC .............. *G06N 3/08* (2013.01); *G06T 11/003* (2013.01); *G16H 30/40* (2018.01); *G06T 2207/10088* (2013.01); *G06T 2207/20081* (2013.01); *G06T 2207/20084* (2013.01); *G06T 2207/30101* (2013.01)

(58) Field of Classification Search
  CPC ........ G06N 3/08; G06N 3/088; G06T 11/003; G06T 2207/10088; G06T 2207/20081; G06T 2207/20084; G06T 2207/30101; G06T 7/0012; G16H 30/40; G16H 50/20; G16H 50/70
  See application file for complete search history.

(56) References Cited

OTHER PUBLICATIONS

Capsule Networks Against Medical Imaging Data Challenges; Amelia Jimenez-Sanchez, Shadi Albarqonni, Diana Mateus; BCN MedTech, DTIC, Universitat Pompeu Fabra, Spain; arXiv:1807.07559v1; Jul. 1, 2018; 10 pages.

Joint Optic Disc and Cup Segmentation Using Fully Convolutional and Adversarial Networks; Sharath M. Shankaranarayana, Keerthi Ram, Kaushik Mitra, and Mohanasankar Sivaprakasam; Dept of Electrical Engineering, IT-Madras, Chennai, India; Healthcare Technology Innovation Centre, IIT-Madras, Chennai, India; Springer International Publishing AG 2017; M.J. Cardoso et al. (Eds ): FIFI/OMIA 2017, LNCS 10554, pp .168-176, 2017.

Unsupervised Anomaly Detection with Generative Adversarial Networks to Guide Marker Discovery; Thomas Schlegl, Philipp Seebock, Sebastian M. Waldstein, Ursula Schmidt-Erfurth, and George Langs; Computational Imaging Research Lab, Department of Ophthalmology and Optometry, Medical University Vienna, Vienna, Austria; Springer International Publishing AG 2017; M. Niethammer et al. (Eds.): IPMI 2017, LNCS 10265; pp. 146-157, 2017.

Unsupervised Learning for Cell-Level Visual Representation in Histopathology Images With Generative Adversarial Networks; Bo Hu, Ye Tang, Eric I-Chao Chang; Yubo Fan, Maode Lai, and Yan Xu; IEEE Journal of Biomedical and Health Informatics, vol. 23, No. 3, May 2019, pp. 1316-1328.

* cited by examiner

METHOD AND DEVICE OF PROCESSING PLAQUES IN MAGNETIC RESONANCE IMAGING OF VESSEL WALL, AND COMPUTER DEVICE

CROSS-REFERENCE TO RELATED APPLICATIONS

The present application is a Continuation-in-Part of PCT/CN2019/078890, filed on Mar. 20, 2019, which claims priority to Chinese patent application No. 201810818827.1, filed on Jul. 24, 2018 and entitled "Method and Device of Treating Plaque From Magnetic Resonance Vascular Wall Imaging," the entire disclosures of which are incorporated herein by reference in their entireties.

BACKGROUND

1. Technical Field

The present disclosure relates to the technical field of image processing, and particularly to a method of processing plaques in magnetic resonance imaging of vessel wall, a device of processing plaques in magnetic resonance imaging of vessel wall, and a computer device.

2. Related Art

Magnetic resonance imaging of vessel wall may not only perform quantitative analysis on vascular plaques of the whole body such as intracranial artery, carotid artery and aorta, but also recognize instability characteristics such as fiber cap of vulnerable plaques, bleeding, calcification, lipid nucleus, inflammation and the like accurately, it is the currently recognized best plaques imaging method. However, since data volume of three-dimensional high-resolution magnetic resonance imaging of vessel wall is huge, the number of images of each inspector may reach 500, so that an experienced professional needs to take 30 minutes to complete the diagnosis of one inspector.

The deep learning method applied in the medical field is a convolutional neural network, and the application field of the convolutional neural network includes medical image treatment, medical image recognition and classification, and the like. Researches of deep learning in medical image recognition and segmentation are mostly based on traditional convolutional neural network algorithms. However, image details may not be excellently processed by the deep learning method based on the convolutional neural network due to loss of information. In the classification problem, the convolutional and full-connectivity-based classification network have developed into a mature network structure, however, the accuracy of classification is still not high.

As described above, there exists a deficiency of low efficiency and low accuracy in recognition and classification of plaques in magnetic resonance imaging of vessel wall in the existing methods.

SUMMARY

A purpose of the present disclosure is providing a method and device of processing plaques in magnetic resonance imaging of vessel wall, and a computer device to recognize and classify plaques in magnetic resonance imaging of vessel wall high efficiently and accurately.

In a first aspect, embodiments of the present disclosure provide a method of processing plaques in magnetic resonance imaging of vessel wall implemented by a computer device, including:

training, by the computer device, a generative adversarial network and a capsule neural network so as to obtain a trained generator network and a trained capsule neural network; and cascade-connecting, by the computer device, the trained generator network with the capsule neural network into a system, to recognize and classify the plaques in magnetic resonance imaging of vessel wall.

In a second aspect, embodiments of the present disclosure provide a network of processing plaques in magnetic resonance imaging of vessel wall, including a generative adversarial network and a capsule neural network;

where the generative adversarial network is configured to recognize plaques in magnetic resonance imaging of vessel wall after being trained, and the capsule neural network is configured to classify the plaques in magnetic resonance imaging of vessel wall.

In a third aspect, embodiments of the present disclosure provide a computing device, including a memory, a processor and a computer program stored in the memory and executable on the processor, where when executing the computer program, the processor is configured to implement steps in the method described as follows:

training a generative adversarial network and a capsule neural network so as to obtain a trained generator network and a trained capsule neural network; and cascade-connecting the trained generator network with the capsule neural network into a system, to recognize and classify the plaques in magnetic resonance imaging of vessel wall.

In a fourth aspect, embodiments of the present disclosure provide a computer readable storage medium which stores a computer program, where when the computer program is executed by a processor, steps of training a generative adversarial network and a capsule neural network so as to obtain a trained generator network and a trained capsule neural network, and cascade-connecting the trained generator network with the capsule neural network into a system so as to recognize and classify the plaques in magnetic resonance imaging of vessel wall in the method are implemented.

It may be seen from the technical solutions of the present disclosure that, in one aspect, since the generative adversarial network includes a capsule neural network, as compared to the traditional convolutional neural network or a fully-connected layer neural network which uses scalar to represent the vascular plaques, the capsule neural network has more abundant vascular plaques characteristic information represented by the vector; in another aspect, as compared to the traditional deep learning algorithm which adopts a gradient propagation method, the capsule neural network uses the dynamic routing algorithm to learn and update the network, thus, the accuracy of recognition and classification of the plaques may be greatly improved when the trained generator network and the capsule neural network are cascaded into a system to recognize and classify the plaques in magnetic resonance imaging of vessel wall.

BRIEF DESCRIPTION OF THE DRAWINGS

These and other features and advantages of the invention will be better understood when considered in connection with the following detailed description and drawings, in which.

DETAILED DESCRIPTION OF THE EMBODIMENTS

In order to make the purpose, the technical solution and the advantageous effects of the present disclosure be clearer and more understandable, the present disclosure will be further described in detail below with reference to accompanying figures and embodiments. It should be understood that the specific embodiments described herein are merely intended to illustrate but not to limit the present disclosure.

In the following description, in order to describe but not intended to limit, concrete details such as specific system structure, technique and so on are proposed, so that comprehensive understanding of the embodiments of the present disclosure is facilitated. However, it will be apparent to the ordinarily skilled one in the art that, the present disclosure may also be implemented in some other embodiments without these concrete details. In some other conditions, detailed explanations of method, circuit, device and system well known to the public are omitted, so that unnecessary details may be prevented from obstructing the description of the present disclosure.

Figure 1:
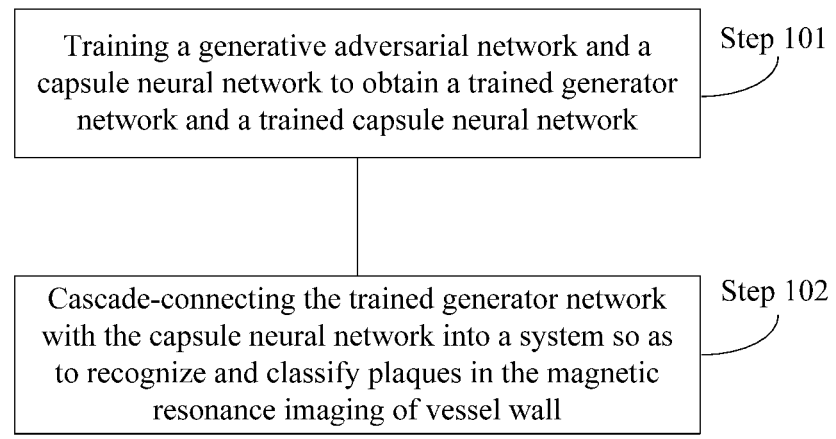
FIG. 1 illustrates a schematic flowchart of implementation of a method of processing plaques in magnetic resonance imaging of vessel wall provided by one embodiment of the present disclosure.

FIG. 1 is a schematic flowchart of implementation of a method of processing plaques in magnetic resonance imaging of vessel wall according to an embodiment of the present disclosure, the method mainly includes the following step S101 and step S102, which are described in detail below:

In a step of S101, training a generative adversarial network and a capsule neural network so as to obtain a trained generator network and a trained capsule neural network.

In this embodiment of the present disclosure, the generative adversarial network includes a discriminator network and a generator network, where the discriminator network applies a hybrid structure of conventional neural network (e.g., convolutional neural network, etc.) and the capsule neural network, and includes a convolutional layer, a PrimaryCaps layer and a DigitCaps layer, the generator network is a deep convolutional network, and the generator network adopts a residual network structure in consideration for more effectively training the deep network; a parametric rectified linear unit may be used as an activation function in the discriminator network and the generator network. The capsule neural network is similar to the discriminator network, the capsule neural network also includes a convolutional layer, a PrimaryCaps layer, and a DigitCaps layer, where the PrimaryCaps layer is computationally equivalent to the conventional convolutional layer, but differs from the conventional convolutional layer in deep sense, this is because the internal part of each capsule in the PrimaryCaps layer is consisted of a plurality of feature vectors, a capsule neuron of the capsule neural network uses a squashing function as the activation function and a dynamic routing updating algorithm is used for training the capsule neuron, however, the convolutional neuron uses a rectified linear unit as the activation function and uses a Adam algorithm to train the conventional convolutional neuron; where the squashing function is expressed as follows:

$$(I^G)v_j = \frac{\|s_j\|^2}{1+\|s_j\|^2} \frac{s_j}{\|s_j\|}$$

Where $s_j$ is the total input of the capsule neural network, and its computational formula is expressed as follows:

$$s_j = \sum_i c_{ij}\hat{u}_{j|i}$$

Where parameter $c_{ij}$ is updated by dynamic routing algorithm, $\hat{u}_{j|i}$ is the information transmitted from the ith capsule neuron to the jth capsule neuron in the following layer, and the computational formula of $\hat{u}_{j|i}$ is expressed as follows:

$$\hat{u}_{j|i} = W_{ij}u_i$$

Where parameter $W_{ij}$ is obtained by the dynamic routing updating algorithm by learning, $u_i$ is the original output of the capsule neuron in the upper layer.

In order to make the generator network and the capsule neural network obtained after training to be higher in recognition rate and precision, and to reduce computational resources as much as possible simultaneously, as one embodiment of the present disclosure, training a generative adversarial network and a capsule neural network to obtain a trained generator network and a trained capsule neural network may be implemented by taking three-dimensional local magnetic resonance imaging of vessel wall as training data, and using the Adam training algorithm and the dynamic routing updating algorithm to generate the adversarial network and the capsule neural network so as to obtain the trained generator network and the trained capsule neural network.

It should be noted that, in order to satisfy K-Lipschitz assumption of Wasserstein distance, this project uses a gradient penalty to satisfy the Lipschitz condition, and the loss function used for training the discriminator network during training of the generative adversarial network and the capsule neural network may be $L(\theta_D)=E_{\tilde{x}\sim P_g}[D_{\theta_D}(\tilde{x})]-E_{x\sim P_r}[D_{\theta_D}(x)]+\lambda E_{\hat{x}\sim P_{\hat{x}}}[(\|\nabla_{\hat{x}} D_{\theta_D}(\tilde{x})\|_2-1)^2]$, the loss function used for training the generator network may be expressed as $L(\theta_G)=L_{MSE}(I^L, I^G)+10^{-4}L_{WANG}(I^G)$, where $D_{\theta_D}$ is the discriminator of parameter $\theta_D$, x is magnetic resonance imaging of vessel wall data, $\tilde{x}$ is the data obtained after the magnetic resonance imaging data of vessel wall is segmented by the generator network, $\hat{x}=\varepsilon x+(1-\varepsilon)\tilde{x}$ is a random sample of random obedience distribution, $\varepsilon$ is a random value of uniform distribution ranged from 0 to 1, $L_{MSE}(I^L, I^G)$ is calculated according to the formula of $$L_{MSE}(I^L, I^G) = \frac{1}{w \times h}\sum_{x=1}^{w}\sum_{y=1}^{h}(I^L_{x,y} - I^G_{x,y})^2,$$

$L_{WANG}(I^G)$ is calculated according to the formula of $L_{WANG}(\theta_G)=-E_{\tilde{x}\sim P_g}[D_{\theta_D}(\tilde{x})]$, where $I^L$ and $I^G$ are segmentation label of magnetic resonance and segmentation output of magnetic resonance of the generator, respectively.

In a step of S102, cascade-connecting the trained generator network with the trained capsule neural network into a system to recognize and classify the plaques in magnetic resonance imaging of vessel wall.

The trained generator network and the trained capsule neural network are cascaded into the system, which actually equalizes to the process of merging the training generator network with the capsule neural network and extracting parameters from the trained generator network and the trained capsule neural network. The merged system may realize integration of recognition and classification of the plaques in magnetic resonance imaging of vessel wall, where the trained generator network is responsible for recognizing the plaques from the magnetic resonance image of vessel wall, and the trained capsule neural network is responsible for classifying the plaques in magnetic resonance imaging of vessel wall.

It may be known from the example of the method of processing plaques in magnetic resonance imaging of vessel wall shown in FIG. 1 that, in one aspect, since the generative adversarial network includes a capsule neural network, as compared to the traditional convolutional neural network or a fully-connected layer neural network which uses scalar to represent the vascular plaques, the capsule neural network has more abundant vascular plaque characteristic information represented by the vector; in another aspect, as compared to the traditional deep learning algorithm which adopts a gradient propagation method, a capsule neural network uses the dynamic routing algorithm to learn and update the network, thus, the accuracy of recognition and classification of the plaques may be greatly improved when the trained generator network and the capsule neural network are cascaded into a system to recognize and classify the plaques in magnetic resonance imaging of vessel wall.

Figure 2:
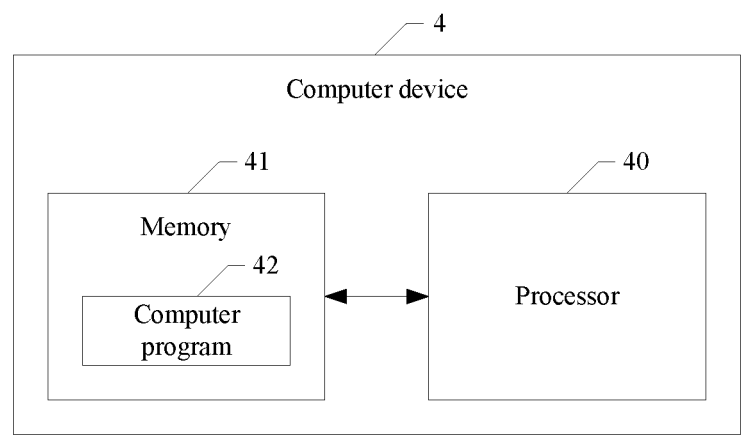
FIG. 2 illustrates a schematic structural block diagram of a computer device provided by one embodiment of the present disclosure.

FIG. 2 illustrates a schematic structural block diagram of a computer device 4 according to an embodiment of the present disclosure. As shown in FIG. 4, the computer device 4 in this embodiment includes a processor 40, a memory 41, and a computer program 42 stored in the memory 41 and executable on the processor 40, such as a program of a method of processing plaques in magnetic resonance imaging of vessel wall. The processor 40 implement the steps in the embodiment of the method of processing plaques in magnetic resonance imaging of vessel wall described above when executing the computer program 42, such as the steps S101 and S102 shown in FIG. 1.

Exemplarily, computer program 42 of the method of processing plaques in magnetic resonance imaging of vessel wall mainly includes: training a generative adversarial network and a capsule neural network so as to obtain a trained generator network and a trained capsule neural network; cascade-connecting the trained generator network with the capsule neural network into a system to recognize and classify plaques in magnetic resonance imaging of vessel wall. The computer program 42 may be divided into one or a plurality of modules/units, the one or plurality of modules/units are stored in a memory 41 and are executed by the processor 40 so as to implement the present disclosure. The one or plurality of modules/units may be a series of computer program instruction segments that may accomplish particular functionalities, these instruction segments are used for describing an executive process of the computer program 42 in the computer device 4. The computer device 4 may include but is not limited to: the processor 40 and a memory 41. It may be understood by the person of ordinary skill in the art that, FIG. 4 is merely an example of the computer device 4, and is not constituted as limitation to the computing device 4, more or less components shown in FIG. 4 may be included, or some components or different components may be combined; for example, the computer device 4 may also include an input and output device, a network access device, a bus, etc.

The so called processor 40 may be CPU (Central Processing Unit), and may also be other general purpose processor, DSP (Digital Signal Processor), ASIC (Application Specific Integrated Circuit), FGPA (Field-Programmable Gate Array), or some other programmable logic devices, discrete gate or transistor logic device, discrete hardware component, etc. The general purpose processor may be a microprocessor, as an alternative, the processor may also be any conventional processor and so on.

The memory 41 may be an internal storage unit of the computing device 4, such as a hard disk or a memory of the computer device 4. The memory 41 may also be an external storage device of the computer device 4, such as a plug-in hard disk, a SMC (Smart Media Card), a SD (Secure Digital) card, a FC (Flash Card) equipped on the computer device 4. Further, the memory 41 may not only include the internal storage unit of the computer device 4 but also include the external storage device of the computer device 4. The memory 41 is configured to store the computer program, and other procedures and data needed by the computer device 4. The memory 41 may also be configured to store data that has been output or being ready to be output temporarily.

In the aforesaid embodiments, the descriptions of each of the embodiments are emphasized respectively, regarding the part of one embodiment which isn't described or disclosed in detail, reference may be made to relevant descriptions in some other embodiments.

The person of ordinary skill in the art may be aware of that, the elements and algorithm steps of each of the examples described in connection with the embodiments disclosed herein may be implemented in electronic hardware, or in combination with computer software and electronic hardware. Whether these functions are implemented by hardware or software depends on the specific application and design constraints of the technical solution. The skilled people could use different methods to implement the described functions for each particular application, however, such implementations should not be considered as going beyond the scope of the present disclosure.

It should be understood that, in the embodiments of the present disclosure, the disclosed device/computer device 4 and method could be implemented in other ways. For example, the device described above are merely illustrative; for example, the division of the units is only a logical function division, and other division could be used in the actual implementation, for example, multiple units or components could be combined or integrated into another system, or some features may be ignored or not performed. In another aspect, the coupling or direct coupling or communicating connection shown or discussed could be an indirect coupling or a communicating connection through some interfaces, devices or units, and the coupling or direct coupling or communicating connection could be electrical, mechanical, or in other form.

The units described as separate components could or could not be physically separate, the components shown as units could or could not be physical units, which may be located in one place, or may be distributed to multiple network elements. A part or a whole of the elements could be selected according to the actual needs to achieve the objective of the present embodiment.

In addition, the various functional units in each of the embodiments of the present disclosure may be integrated into a single processing unit, or exist individually and physically, or two or more than two units are integrated into a single unit. The aforesaid integrated unit may either be achieved by hardware, or be achieved in the form of software functional units.

If the integrated unit is achieved in the form of software functional units, and is sold or used as an independent product, it may be stored in a computer readable storage medium. Based on this understanding, a whole or part of flow process of implementing the method in the aforesaid embodiments of the present disclosure may also be accomplished by using computer program to instruct relevant hardware. The computer program of the method of processing plaques in magnetic resonance imaging of vessel wall may be stored in a computer readable storage medium, when the computer program is executed by the processor, the steps in the various method embodiments described above, that is, training a generative adversarial network and a capsule neural network so as to obtain a trained generator network and a trained capsule neural network; and cascade-connecting the trained generator network with the capsule neural network into a system to recognize and classify plaques in magnetic resonance imaging of vessel wall may be implemented. Where, the computer program includes computer program codes which may be in the form of source code, object code, executable documents or some intermediate form, etc. The computer readable medium may include: any entity or device that may carry the computer program codes, recording medium, USB flash disk, mobile hard disk, hard disk, optical disk, computer storage device, ROM (Read-Only Memory), RAM (Random Access Memory), electrical carrier signal, telecommunication signal and software distribution medium, etc. It needs to be explained that, the contents contained in the computer readable medium may be added or reduced appropriately according to the requirement of legislation and patent practice in a judicial district, for example, in some judicial districts, according to legislation and patent practice, the computer readable medium doesn't include electrical carrier signal and telecommunication signal.

The aforesaid embodiments are only intended to explain but not to limit the technical solutions of the present disclosure. Although the present disclosure has been explained in detail with reference to the above-described embodiments, the person of ordinary skill in the art may understand that, the technical solutions described in each of the embodiments mentioned above may still be amended, or some technical features in the technical solutions may be replaced equivalently; these amendments or equivalent replacements, which doesn't cause the essence of the corresponding technical solution to be broken away from the spirit and the scope of the technical solution in various embodiments of the present disclosure, should all be included in the protection scope of the present disclosure.

What is claimed is:

1. A method of processing plaques in magnetic resonance imaging of vessel wall implemented by a computer device comprising a memory, a processor and a computer program stored in the memory and executable on the processor, the method comprising:
    training, by the processor of the computer device, a generative adversarial network and a capsule neural network, to obtain a trained generator network and a trained capsule neural network; and
    cascade-connecting, by the processor of the computer device, the trained generator network with the capsule neural network into a system to recognize and classify the plaques in magnetic resonance imaging of vessel wall;

wherein the generative adversarial network comprises a discriminator network and a generator network, a loss function used for training the discriminator network is expressed as $L(\theta_D)=E_{\tilde{x} \sim P_g}[D_{\theta_D}(\tilde{x})]-E_{x \sim P_r}[D_{\theta_D}(x)]+\lambda E_{\hat{x} \sim P_{\hat{x}}}[(\|\nabla_{\hat{x}} D_{\theta_D}(\hat{x})\|_2-1)^2]$, a loss function used for training the generator network is expressed as $L(\theta_G)=L_{MSE}(I^L, I^G)+10^{-4}L_{WANG}(I^G)$, wherein $D_{\theta_D}$ is a discriminator of parameter $\theta_D$, the x is magnetic resonance imaging data of vessel wall, the $\tilde{x}$ is data obtained after the magnetic resonance imaging data of vessel wall is segmented by the generator network, the $\hat{x}=\epsilon x+(1-\epsilon)\tilde{x}$ is a random sample of random obedience distribution, the $\epsilon$ is random value of uniform distribution ranged from 0 to 1, the $L_{MSE}(I^L, I^G)$ is calculated according to a formula of $$L_{MSE}(I^L, I^G) = \frac{1}{w \times h} \sum_{x=1}^{w} \sum_{y=1}^{h} (I^L_{x,y} - I^G_{x,y})^2,$$

and the $L_{WANG}(I^G)$ is calculated according to a formula of $L_{WANG}(\theta_G)=-E_{\tilde{x} \sim P_g}[D_{\theta_D}(\tilde{x})]$.

2. The method according to claim 1, wherein the step of training a generative adversarial network and a capsule neural network so as to obtain a trained generator network and a trained capsule neural network comprising:
    taking three-dimensional local magnetic resonance imaging of vessel wall as training data, and using Adam training algorithm and dynamic routing updating algorithm to train the generative adversarial network and the capsule neural network so as to obtain the trained generator network and the trained capsule neural network, by the processor of the computer device.

3. A network of processing plaques in magnetic resonance imaging of vessel wall, comprising a generative adversarial network and a capsule neural network;
    wherein the generative adversarial network is configured to recognize plaques in magnetic resonance imaging of vessel wall after being trained, and the capsule neural network is configured to classify the plaques in magnetic resonance imaging of vessel wall;
    wherein the generative adversarial network comprises a discriminator network and a generator network, the generator network is a deep convolutional network using a residual network structure, a hybrid structure of the traditional neural network and the capsule neural network is adopted by the discriminator network, the discriminator network or the capsule neural network comprises a convolutional layer, a PrimaryCaps layer and a DigitCaps layer, a loss function used for training the discriminator is expressed as $L(\theta_D)=E_{\tilde{x} \sim P_g}[D_{\theta_D}(\tilde{x})]-E_{x \sim P_r}[D_{\theta_D}(x)]+\lambda E_{\hat{x} \sim P_{\hat{x}}}[(\|\nabla_{\hat{x}} D_{\theta_D}(\hat{x})\|_2-1)^2]$, a loss function used for training the generator network is expressed as $L(\theta_G)=L_{MSE}(I^L, I^G)+10^{-4}L_{WANG}(I^G)$, wherein the $D_{\theta_D}$ is a discriminator of parameter $\theta_D$, the x is magnetic resonance imaging data of vessel the $\tilde{x}$ is data obtained after the magnetic resonance imaging data of vessel wall is segmented by the generator network, the $\hat{x}=\epsilon x+(1-\epsilon)\tilde{x}$ is a random sample of random obedience distribution, the $\epsilon$ is a random value of uniform distribution ranged from 0 to 1, the $L_{MSE}(I^L, I^G)$ is calculated according to a formula of $$L_{MSE}(I^L, I^G) = \frac{1}{w \times h} \sum_{x=1}^{w} \sum_{y=1}^{h} (I^L_{x,y} - I^G_{x,y})^2,$$

and the $L_{WANG}(I^G)$ is calculated according to a formula of $L_{WANG}(\theta_G)=-E_{\tilde{x} \sim P_g}[D_{\theta_D}(\tilde{x})]$.

4. A computer device, comprising a memory, a processor and a computer program stored in the memory and executable on the processor, wherein the processor is configured to implement steps in the method according to claim 1, when executing the computer program.

\* \* \* \* \*